US011172834B2

(12) United States Patent
Sawanoi et al.

(10) Patent No.: US 11,172,834 B2
(45) Date of Patent: Nov. 16, 2021

(54) SENSOR ASSEMBLY

(71) Applicant: OMRON HEALTHCARE CO., LTD., Muko (JP)

(72) Inventors: Yukiya Sawanoi, Kyoto (JP); Yoshihiko Sano, Kyoto (JP); Takeshi Kubo, Kyoto (JP); Toshihiko Ogura, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 250 days.

(21) Appl. No.: 16/199,364

(22) Filed: Nov. 26, 2018

(65) Prior Publication Data

US 2019/0090762 A1 Mar. 28, 2019

Related U.S. Application Data

(63) Continuation of application No. PCT/JP2017/017269, filed on May 2, 2017.

(30) Foreign Application Priority Data

May 27, 2016 (JP) .............................. JP2016-106625

(51) Int. Cl.
*A61B 5/022* (2006.01)
*A61B 5/021* (2006.01)
*A61B 5/00* (2006.01)

(52) U.S. Cl.
CPC .......... *A61B 5/02233* (2013.01); *A61B 5/022* (2013.01); *A61B 5/02141* (2013.01); *A61B 5/02225* (2013.01); *A61B 5/681* (2013.01)

(58) Field of Classification Search
CPC . A61B 5/02233; A61B 5/022; A61B 5/02141; A61B 5/02225; A61B 5/681
See application file for complete search history.

(56) References Cited

U.S. PATENT DOCUMENTS

| 6,336,901 | B1 | 1/2002 | Itonaga et al. |
| 2006/0116588 | A1* | 6/2006 | Archibald .......... A61B 5/02233 600/494 |

(Continued)

FOREIGN PATENT DOCUMENTS

| CN | 101909521 A | 12/2010 |
| CN | 101346100 B | 4/2011 |

(Continued)

OTHER PUBLICATIONS

Sep. 29, 2020 Office Action issued in Chinese Patent Application No. 201780032639.X.

(Continued)

*Primary Examiner* — Devin B Henson
*Assistant Examiner* — Justin Xu
(74) *Attorney, Agent, or Firm* — Oliff PLC

(57) ABSTRACT

A sensor assembly of the present invention includes a fluid chamber. A pressure transmitting fluid disposed facing an artery passing portion of a part to be measured via a film which forms a part of an outer wall of the fluid chamber is accommodated in the fluid chamber. A pressure sensor is provided for detecting pressure of the pressure transmitting fluid as pressure applied to the artery passing portion of the part to be measured. Plate members each having a flat shape along a longitudinal direction of a wrist as the part to be measured are disposed on a side opposite to the part to be measured along the film.

10 Claims, 12 Drawing Sheets

(56) References Cited

U.S. PATENT DOCUMENTS

| | | | | |
|---|---|---|---|---|
| 2007/0287923 | A1* | 12/2007 | Adkins | A61B 5/02405 600/485 |
| 2008/0045866 | A1* | 2/2008 | Rastegar | A61H 9/0092 601/9 |
| 2020/0305740 | A1* | 10/2020 | Quan | A61B 5/6844 |

FOREIGN PATENT DOCUMENTS

| | | |
|---|---|---|
| CN | 104434053 A | 3/2015 |
| CN | 104739387 A | 7/2015 |
| CN | 104825144 A | 8/2015 |
| EP | 1214904 A2 | 6/2002 |
| JP | S59-18052 B2 | 4/1984 |
| JP | H02-82305 U | 6/1990 |
| JP | H11-309119 A | 11/1999 |
| JP | 2005-342163 A | 12/2005 |
| JP | 2009-284967 A | 12/2009 |
| JP | 2012-152372 A | 8/2012 |
| JP | 2013-215397 A | 10/2013 |
| JP | 2014-166561 A | 9/2014 |
| WO | 2015/122100 A1 | 8/2015 |

OTHER PUBLICATIONS

Jul. 25, 2017 International Search Report issued in International Patent Application No. PCT/JP2017/017269.
Apr. 2, 2021 Office Action issued in Chinese Patent Application No. 201780032639.X.
Jul. 4, 2017 International Search Report issued in International Patent Application No. PCT/JP2017/017266.
Dec. 23, 2020 Office Action Issued in U.S. Appl. No. 16/199,390.
Sep. 29, 2020 Office Action issued in Chinese Patent Application No. 201780032638.5.
Apr. 2, 2021 Office Action issuesd in Chinese Patent Application No. 201780032638.5.
Jun. 21, 2021 U.S. Office Action issued U.S. Appl. No. 16/199,390.

* cited by examiner

CASE WHERE OUTPUT OF SECOND PRESSURE SENSOR IS USED

CASE WHERE OUTPUT OF FIRST PRESSURE SENSOR IS USED

SENSOR ASSEMBLY

CROSS-REFERENCE TO RELATED APPLICATIONS

This is a continuation application of International Application No. PCT/JP2017/017269, with an International filing date of May 2, 2017, which claims priority of Japanese Patent Application No. 2016-106625 filed on May 27, 2016, the entire content of which is hereby incorporated by reference.

TECHNICAL FIELD

The present invention relates to a sensor assembly, and more particularly to a sensor assembly for detecting pressure of a part to be measured. The sensor assembly is typically incorporated in a blood pressure measuring cuff and is used to measure blood pressure of the part to be measured.

BACKGROUND ART

Conventionally, as this kind of sphygmomanometer, as disclosed in, for example, Patent Literature 1 (JP 2013-215397 A), a sphygmomanometer having a blood pressure measuring cuff to be wrapped around a wrist as a part to be measured and a main body integrally attached to the cuff is known. In this sphygmomanometer, pressure in a pressurizing air bag contained in the cuff is detected by a pressure sensor mounted on the main body. At a time of blood pressure measurement, in a state where the cuff is worn by surrounding the wrist, pressurizing air is supplied from a pump mounted on the main body to the air bag and an artery of the wrist is pressed. Then, based on an output of the pressure sensor, a blood pressure measurement value is obtained by an oscillometric method.

SUMMARY OF INVENTION

Incidentally, due to a recent health-oriented boom, there is a growing need to measure blood pressure with a sphygmomanometer (a blood pressure measuring cuff) always worn on a wrist. In that case, in the viewpoints of appearance, comfort of wearing, etc., it is desired to make a width direction dimension of a cuff (a dimension in a direction along a longitudinal direction of a wrist, hereinafter referred to as "cuff width dimension") as small as possible.

However, when the cuff width dimension is set to be as small as, for example, about 25 mm in the sphygmomanometer, the cuff (an air bag) greatly expands in a thickness direction at a time of pressurization, its cross section becomes close to a circular shape from a flat elliptical shape, and compression loss occurs. In other words, pressure in the cuff is higher than pressure applied to an artery of the wrist. As a result, there is a problem that a blood pressure measurement value is observed higher than actual blood pressure and a measurement error becomes large.

This problem may be solved by providing, separately from a pressing cuff which presses a part to be measured, a means for detecting pressure applied to an artery passing portion of the part to be measured by the pressing cuff.

Therefore, an object of the present invention is to provide a sensor assembly suitable for detecting pressure applied to an artery passing portion of a part to be measured by a pressing cuff, separately from the pressing cuff that presses the part to be measured.

In order to solve the above problem, the present disclosure provides a sensor assembly, in a blood pressure measuring cuff including a pressing cuff which is belt-like, wound around a part to be measured, and receives supply of a pressurizing fluid to press the part to be measured, and the sensor assembly disposed at a portion of an inner peripheral surface of the pressing cuff which should face an artery of the part to be measured to detect pressure applied to an artery passing portion of the part to be measured by the pressing cuff, separately from the pressing cuff, the sensor assembly comprising:

a fluid chamber;

a pressure transmitting fluid accommodated in the fluid chamber; and a pressure sensor for detecting pressure of the pressure transmitting fluid as pressure applied to the artery passing portion of the part to be measured, wherein the fluid chamber includes a film that forms a part of an outer wall of the fluid chamber and should be brought into contact with the artery passing portion of the part to be measured, a plate member disposed on a side opposite to the part to be measured along the film and having a flat shape along a longitudinal direction of a wrist serving as the part to be measured, and a cylindrical connecting tube part integrally formed with the plate member and extending from the plate member to a side opposite to the part to be measured, a peripheral edge of the film is welded to a peripheral edge of the plate member, the connecting tube part has a through hole that allows the pressure transmitting fluid to flow across the plate member, the pressure sensor has a main part for detecting the pressure of the pressure transmitting fluid and a cylindrical introduction tube part for guiding the pressure transmitting fluid to the main part, and the introduction tube part of the pressure sensor is fluid-tightly fitted to the connecting tube part directly or via a flexible tube.

In the present specification, the "part to be measured" typically refers to a wrist, but it may be a part other than the wrist (for example, an upper arm). If the part to be measured is a wrist, for example, the "artery passing portion" of the part to be measured refers to a portion through which a radial artery or an ulnar artery passes (including a surface of the wrist).

The "inner peripheral surface" of the pressing cuff refers to a surface, of both surfaces of a belt of the pressing cuff, which faces the part to be measured at the time of wearing.

The "sensor assembly" "to detect pressure applied to an artery passing portion of the part to be measured by the pressing cuff, separately from the pressing cuff" means detecting the pressure itself applied to the artery passing portion of the part to be measured outside the pressing cuff, not the pressure within the pressing cuff (or a space communicating therewith).

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENT

Hereinafter, an embodiment of the present invention will be described in detail with reference to the drawings.
(Configuration of Sphygmomanometer)

Figure 1:
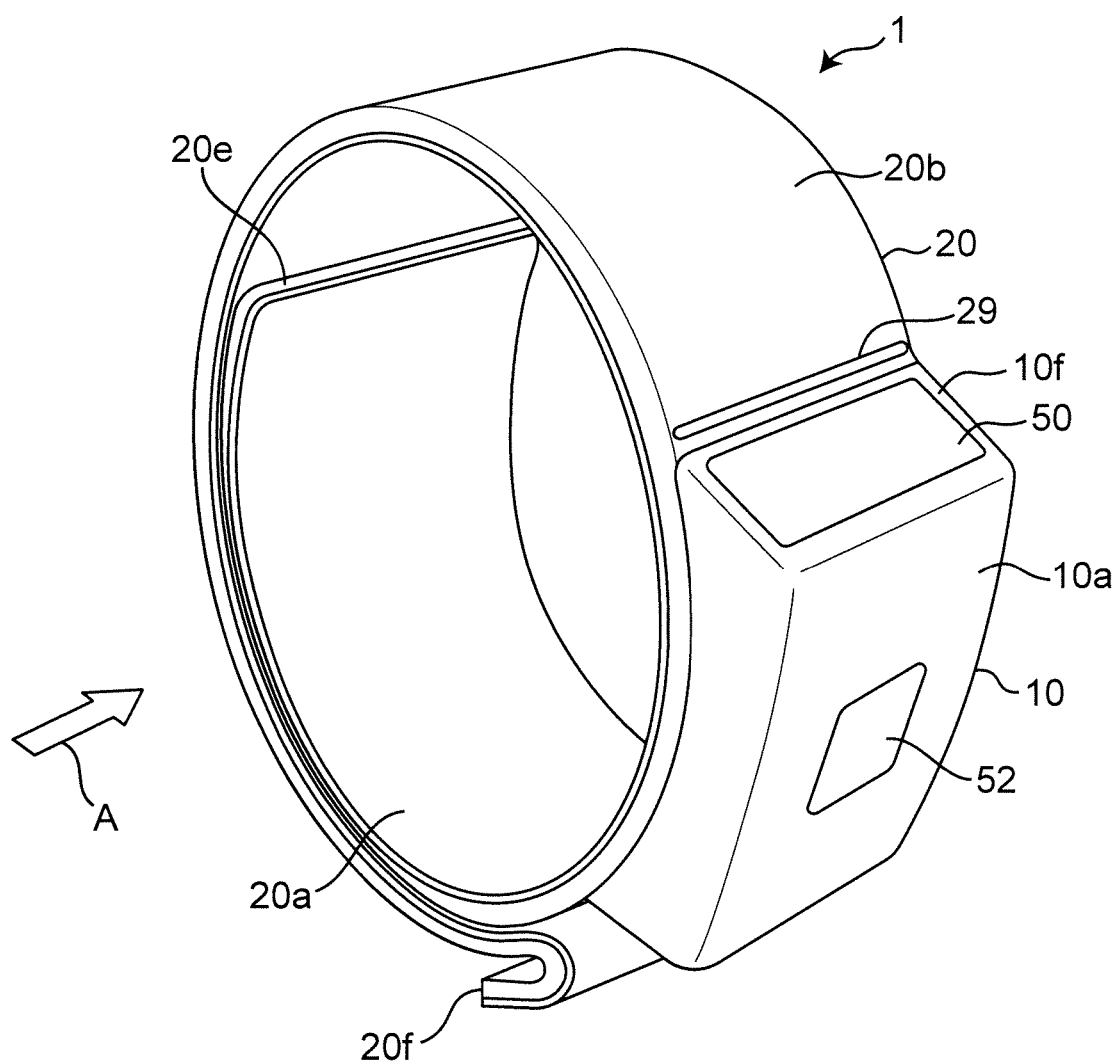
FIG. 1 is a perspective view showing an external appearance of a sphygmomanometer including a blood pressure measuring cuff having a sensor assembly according to an embodiment of the present invention.
Figure 2:
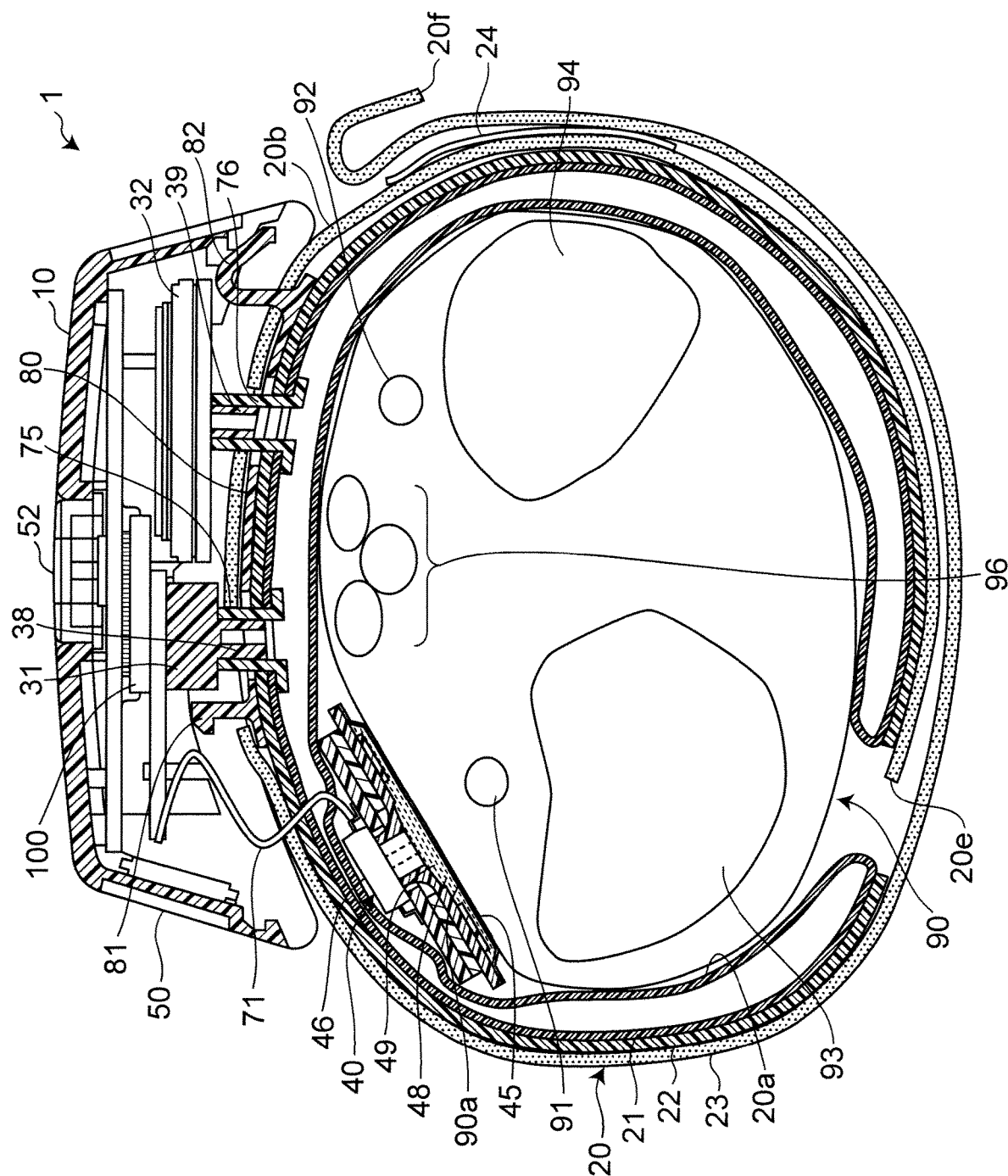
FIG. 2 is a view showing a cross-sectional structure of the sphygmomanometer in a state of being worn on a left wrist.

FIG. 1 shows an appearance of a sphygmomanometer (indicated as a whole by reference numeral 1) including a sensor assembly according to one embodiment of the present invention as seen obliquely. Further, FIG. 2 shows a cross-sectional structure of the sphygmomanometer 1 in a state of being worn (hereinafter referred to as a "worn state") on a left wrist 90 as a part to be measured.

As shown in these figures, the sphygmomanometer 1 roughly includes a blood pressure measuring cuff 20 to be wrapped around the user's left wrist 90 and a main body 10 integrally attached to the cuff 20.

As can be clearly seen in FIG. 1, the cuff 20 has an elongated belt-like shape so as to surround the left wrist 90 along a circumferential direction, and has an inner peripheral surface 20a that should be brought into contact with the left wrist 90 and an outer peripheral surface 20b on a side opposite to the inner peripheral surface 20a. In this example, a dimension in a width direction of the cuff 20 (a cuff width dimension) is set to 25 mm.

The main body 10 is disposed by being integrally attached to a substantially central part between one end 20e and another end 20f in the circumferential direction of the outer peripheral surface 20b of the cuff 20. In this example, the part where the main body 10 is disposed corresponds to a palm side surface (a surface on a palm side) of the left wrist 90 in the worn state (see FIG. 2). Note that, in FIG. 2, a radius 93, an ulna 94, a radial artery 91, an ulnar artery 92, and a tendon 96 of the left wrist 90 are shown.

As can be clearly seen in FIG. 1, the main body 10 has a three-dimensional shape having a thickness in a direction perpendicular to the outer peripheral surface 20b of the cuff 20. The main body 10 is formed to be small and thin so as not to disturb user's daily activities. In this example, the main body 10 has a trapezoidal contour protruding outwardly from the cuff 20, as can be clearly seen in FIG. 2.

As shown in FIG. 1, on a top surface (a surface farthest from the outer peripheral surface 20b of the cuff 20) 10a of the main body 10, an operation unit 52 for inputting an instruction from the user is provided. On a side surface (a side surface on an upper side in FIG. 1) 10f of the main body 10, a display unit 50 forming a display screen is provided.

An alignment mark 29 extending in the width direction along the side surface 10f of the main body 10 is provided on the outer peripheral surface 20b of the cuff 20. This alignment mark 29 is used for aligning a circumference of the left wrist 90 when the sphygmomanometer 1 is worn on the left wrist 90.

As shown in FIG. 2, in this example, the cuff 20 includes an outer cloth 23, a curler 22 attached along an inner peripheral surface of the outer cloth 23, a pressing cuff 21 attached to an inner peripheral surface of the curler 22, and a sensor assembly 40 as an arterial pressure sensor disposed at a portion that should face the radial artery 91 of the left wrist 90 (in other words, a portion corresponding to the alignment mark 29 in FIG. 1), of the inner peripheral surface 20a of the pressing cuff 21 (that is, the inner peripheral surface of the entire cuff 20).

In this example, the outer cloth 23 is made of a substantially non-stretchable cloth, and forms the outer peripheral surface 20b of the cuff 20. In the worn state, the outer cloth 23 is configured so that the one end 20e as an inner peripheral side and the other end 20f as an outer peripheral side in the circumferential direction overlap each other. A hook-and-loop fastener 24 having a large number of fine hooks is attached to an outer surface of a portion of the outer cloth 23 extending from the main body 10 to the one end 20e side. An inner surface of the outer cloth 23 has a large number of fine loops that can engage with those hooks. As a result, the one end 20e side (the inner peripheral side) and the other end 20f side (the outer peripheral side) of the outer cloth 23 can be surely fixed in a state of overlapping each other. Note that the outer cloth 23 may be made not only of cloth but also of one or more layers of resin.

The curler 22 is made of a flexible plastic material. The curler 22 maintains a shape of the cuff 20 (including the pressing cuff 21) in a circular shape in a natural state, thereby facilitating wearing of the cuff 20 on the left wrist 90. The curler 22 and the pressing cuff 21 to be described in detail below are set to have dimensions that make one round of the left wrist 90 in the circumferential direction. Note that the curler 22 can be omitted.

Figure 3A:
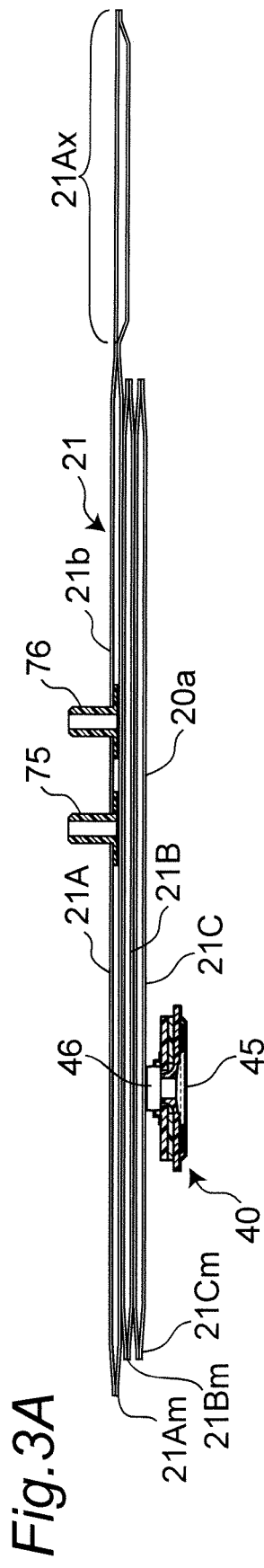
FIG. 3A is a sectional view showing a pressing cuff and a sensor assembly in a deployed state constituting a part of the blood pressure measuring cuff.
Figure 3B:
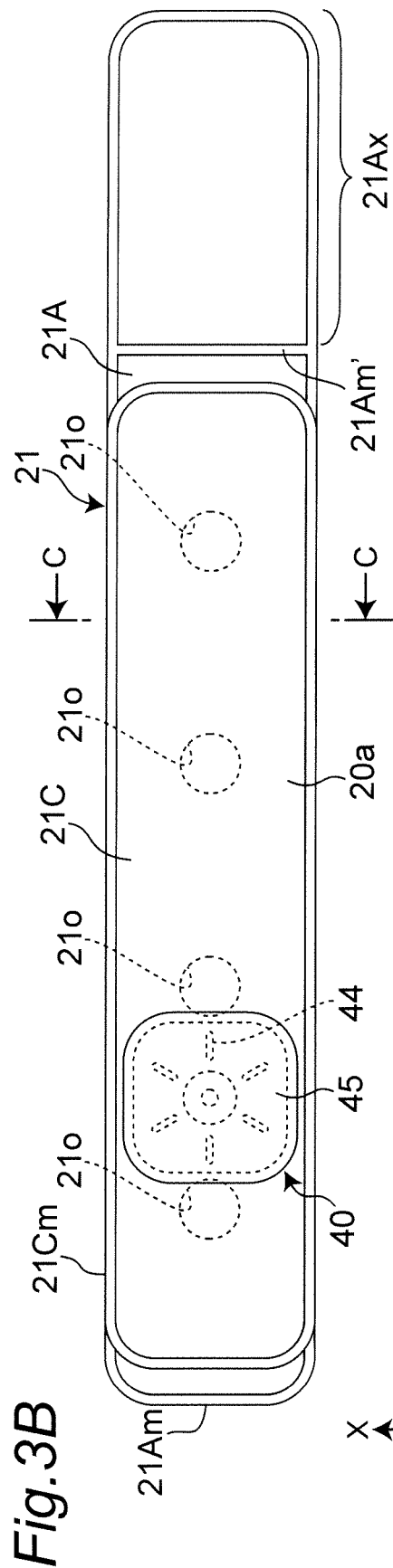
FIG. 3B is a view showing the pressing cuff and the sensor assembly as viewed from below in FIG. 3A.
Figure 3C:
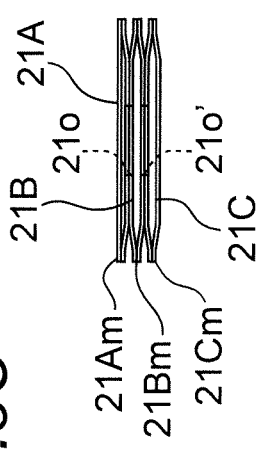
FIG. 3C is a view showing a cross section taken along a line C-C in FIG. 3B.

FIG. 3A shows a cross section of the pressing cuff 21 and the sensor assembly 40 in a deployed state. FIG. 3B shows the pressing cuff 21 and the sensor assembly 40 as viewed from below in FIG. 3A. FIG. 3C shows a cross section taken along a line C-C in FIG. 3B.

As can be seen from FIGS. 3A and 3B, the pressing cuff 21 has a belt-like shape elongated in one direction (a Y direction) as a whole, and has three fluid bags 21A, 21B, and 21C stacked in a thickness direction. Each of the fluid bags 21A, 21B, and 21C is formed by facing two extensible and contractible polyurethane sheets (thickness t=0.15 mm) and welding peripheral edges 21Am, 21Bm, and 21Cm thereof. In this example, a width of the peripheral edge (a welded portion) 21Am, 21Bm, 21Cm is set to 3 mm.

As shown in FIG. 3A, substantially cylindrical nipples 75 and 76 are attached to the fluid bag 21A by penetrating the polyurethane sheet which is on the outer peripheral side in the worn state. Through these nipples 75 and 76, pressurizing fluid (in this example, air) can be supplied from the main body 10 side or exhausted. Further, as can be seen from FIGS. 3B and 3C, between the fluid bag 21A and the adjacent fluid bag 21B, and between the fluid bag 21B and the adjacent fluid bag 21C, the pressurizing fluid (in this example, air) can flow through a plurality of (in this example, four) through holes 21o and 21o', respectively. As a result, when the pressing cuff 21, in the worn state, receives supply of the pressurizing fluid from the main body 10 side through the nipples 75 and 76, the stacked three fluid bags 21A, 21B, and 21C expand so as to compress the left wrist 90 as a whole.

In this example, dimensions in a width direction (an X direction) of the fluid bags 21A, 21B, and 21C are the same and are set to 25 mm. In other words, a dimension in a width direction of the pressing cuff 21 (accordingly, the cuff 20) (a cuff width dimension) is set to 25 mm.

A dimension in the Y direction of the fluid bag 21A on the outer peripheral side in the worn state is set to be larger than dimensions in the Y direction of the remaining fluid bags 21B and 21C. A portion 21Ax of the fluid bag 21A that crosses the fluid bags 21B and 21C in the Y direction is sealed off by a welding line 21Am' extending in the width direction (the X direction). This 21Ax corresponds to a back side surface of the left wrist 90 (a surface on a back of a hand) in the worn state. In this example, the dimension in the Y direction of the fluid bag 21A is set to 185 mm, and the dimensions in the Y direction of the fluid bags 21B and 21C are set to 135 mm.

Figure 4:
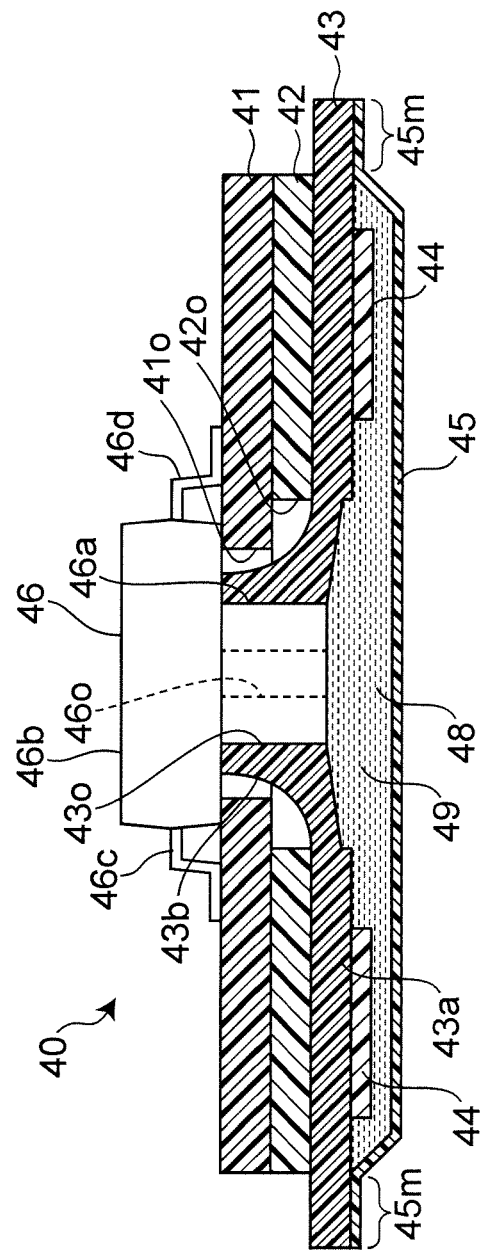
FIG. 4 is a view showing a structure of the sensor assembly in detail.

As shown in FIG. 4, the sensor assembly 40 includes, in an order from a side attached to the inner peripheral surface 20a of the pressing cuff 21, a first pressure sensor 46, a flat wiring substrate 41, a flat reinforcing plate 42 mounted along the wiring substrate 41, a joint member 43, and a film 45.

The first pressure sensor 46 includes a commercially available piezoresistive pressure sensor. The first pressure sensor 46 has a substantially rectangular parallelepiped main part 46b containing a piezoresistive body, a substantially cylindrical introduction tube part 46a for guiding a fluid to the main part 46b, and lead terminals 46c and 46d projecting from the main part 46b and connected to the wiring substrate 41.

Wiring (not shown) for the first pressure sensor 46 is mounted on the wiring substrate 41. A circular through hole 41o is provided substantially in a center of the wiring substrate 41. A wiring line 71 (see FIG. 2) for outputting an output of the first pressure sensor 46 as an electric signal to the main body 10 side extends from the wiring substrate 41. As a result, wiring work from the sensor assembly 40 to the main body 10 is easily performed. Note that, if a connector for wiring connection is provided at a tip of the wiring line 71 and/or in the main body 10, the wiring work is performed more easily. Further, in this example, the output from the sensor assembly 40 to the main body 10 can be achieved with a simple configuration and space saving, compared with a case where pressure is transmitted using piping.

In this example, the reinforcing plate 42 is made of a rigid hard resin having a thickness of about 1 mm, and is provided to increase rigidity of the sensor assembly 40 as a whole. A circular through hole 42o is provided substantially in a center of the reinforcing plate 42 concentrically with the through hole 41o of the wiring substrate 41.

The joint member 43 includes a plate part 43a attached along the reinforcing plate 42 and a substantially cylindrical connecting tube part 43b extending from a substantially center of the plate part 43a to an outer surface (an upper surface in FIG. 4) level of the wiring substrate 41 through the through hole 42o of the reinforcing plate 42 and the through hole 41o of the wiring substrate 41. On a surface of the plate part 43a of the joint member 43 on the film 45 side, a spacer 44 for securing a gap between the plate part 43a and the film 45 is protruded. In this example, as shown in FIG. 3B, six spacers 44 are provided radially.

As shown in FIG. 4, the film 45 is made of a polyurethane sheet (thickness t=0.15 mm) in this example. A peripheral edge 45m of the film 45 is welded to a peripheral edge of the plate part 43a of the joint member 43.

The introduction tube part 46a of the first pressure sensor 46 is fluid-tightly (liquid-tightly in this example) fitted into the connecting tube part 43b of the joint member 43.

As a result, a sealed fluid chamber 48 is constituted by the film 45, the joint member 43, and the introduction tube part 46a and the main part 46b of the first pressure sensor 46. In this fluid chamber 48, a pressure transmitting fluid 49 is accommodated. The fluid 49 is an incompressible fluid, which in this example consists of water or silicone oil.

As shown in FIG. 2, in the worn state, the fluid 49 is disposed facing an artery passing portion (a portion through which the radial artery 91 passes) 90a of the left wrist 90 via the film 45 which forms a part of an outer wall of the fluid chamber 48. The first pressure sensor 46 detects pressure applied to the artery passing portion 90a of the left wrist 90 via the film 45 and the fluid 49.

In this example, the wiring substrate 41, the reinforcing plate 42, and the plate part 43a of the joint member 43 included in the sensor assembly 40 constitute a plate member having a flat shape. For these plate members 41, 42, 43a, a dimension in the circumferential direction (the Y direction in FIG. 3) along the circumference of the left wrist 90 is desirably set within a range of 15 mm to 100 mm, is more desirably set within a range of 15 mm to 60 mm, and further, is more desirably set within a range of 15 mm to 30 mm. Further, a dimension in the width direction (the X direction in FIG. 3) along a longitudinal direction of the left wrist 90 is desirably set within a range of 20 mm to 30 mm, and is more desirably set within a range of 20 mm to 25 mm. As a result, these plate members 41, 42, 43a can appropriately press the artery passing portion 90a of the left wrist 90.

In this example, a portion of the fluid chamber 48 facing the left wrist 90 as the part to be measured is constituted by the film 45 and the plate member (the wiring substrate 41, the reinforcing plate 42 and the plate part 43a of the joint member 43) having the flat shape along the film 45, in particular, in a state in which the peripheral edge 45m of the film 45 and the peripheral edge of the plate part 43a of the joint member 43 are welded to each other. Note that the reinforcing plate 42 may be omitted by assuming a plate material of the wiring substrate 41 as a material made of a rigid hard resin (for example, glass epoxy material). This makes it possible to reduce a dimension in the thickness direction of the sensor assembly 40 (and thus the cuff 20).

In addition, the wiring substrate 41 and the reinforcing plate 42 have the through holes 41o, 42o respectively, and the connecting tube part 43b of the joint member 43 passing through these through holes 41o, 42o works as a through hole through which the fluid 49 can flow. Accordingly, even when the first pressure sensor 46 is disposed on the side opposite to the film 45 with respect to the plate members 41, 42, 43a as in this example, the first pressure sensor 46 can detect the pressure applied to the artery passing portion 90a of the left wrist 90 as pressure of the fluid 49 through the through holes 41o, 42o and the connecting tube part 43b. Therefore, presence of the plate members 41, 42, 43a does not prevent detection of the pressure by the first pressure sensor 46.

As shown in FIG. 2, in the cuff 20, an attachment member 80 is interposed between the outer cloth 23 and the curler 22 at a substantially central part between the one end 20e and the other end 20f in the circumferential direction. The attachment member 80 is a plate-shaped member curved along the curler 22, and has hooks 81, 82 protruding outward in the vicinity of both ends in the circumferential direction of the plate. The main body 10 is integrally attached to the cuff 20 by being engaged with these hooks 81, 82. Thus, it is easy to always wear the sphygmomanometer 1 on the wrist.

The nipples 75, 76 of the pressing cuff 21 penetrate the curler 22, the attachment member 80, and the outer cloth 23 and protrude outward (the main body 10 side). The nipples 75, 76 are fluid-tightly (airtightly in this example) fitted to air pipes 38, 39 of the main body 10.

Note that, when attaching the main body 10 to the cuff 20, the wiring line 71 extending from the sensor assembly 40 bypasses the pressing cuff 21, the curler 22, and the outer cloth 23 and is connected inside the main body 10.

Figure 5:
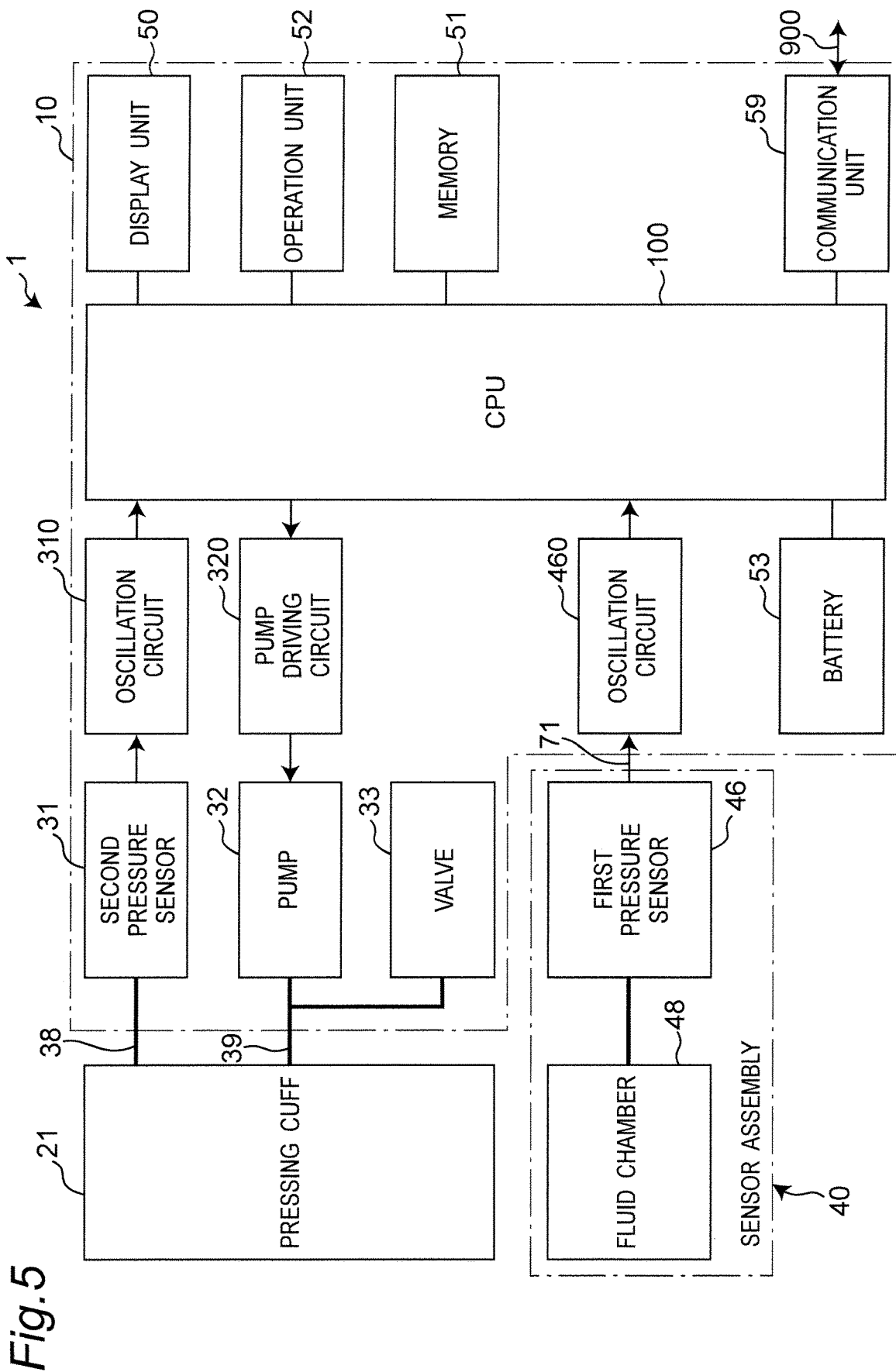
FIG. 5 is a diagram showing a block configuration of a control system of the sphygmomanometer.

FIG. 5 shows a block configuration of the sphygmomanometer 1. As a blood pressure measuring element for executing blood pressure measurement, in addition to the display unit 50 and the operation unit 52 described above, a CPU (Central Processing Unit) 100 as a control unit, a memory 51 as a storage unit, a communication unit 59, a second pressure sensor 31, a pump 32, a valve 33, an oscillation circuit 310 for converting an output from the second pressure sensor 31 into a frequency, and a pump driving circuit 320 for driving the pump 32 are mounted on the main body 10 of the sphygmomanometer 1. Furthermore, an oscillation circuit 460 for converting an output from the first pressure sensor 46 of the sensor assembly 40 into a frequency and a battery 53 are mounted on the main body 10.

In this example, the display unit 50 is composed of an organic EL (Electro Luminescence) display, and displays information related to blood pressure measurement such as a blood pressure measurement result and other information according to a control signal from the CPU 100. Note that the display unit 50 is not limited to the organic EL display, and may be composed of another type of display unit such as an LCD (Liquid Crystal Display), for example.

In this example, the operation unit 52 is composed of a push type switch, and inputs to the CPU 100 an operation signal corresponding to an instruction to start or stop blood pressure measurement by a user. Note that the operation unit 52 is not limited to the push type switch, and may be a pressure sensitive type (resistance type) or a proximity type (capacitance type) touch panel type switch, for example. Further, a microphone (not shown) may be provided and an instruction to start blood pressure measurement may be input by the user's voice.

The memory 51 non-transitorily stores data of a program for controlling the sphygmomanometer 1, data used for controlling the sphygmomanometer 1, setting data for setting various functions of the sphygmomanometer 1, data on a measurement result of a blood pressure value, etc. Further, the memory 51 is used as a work memory or the like when the program is executed.

The CPU 100 executes various functions as the control unit according to the program for controlling the sphygmomanometer 1 stored in the memory 51. For example, when executing a blood pressure measuring function, the CPU 100 performs control to drive the pump 32 (and the valve 33) based on a signal from the second pressure sensor 31 in response to an instruction to start the blood pressure measurement from the operation unit 52. Further, in this example, the CPU 100 performs control to calculate a blood pressure value based on a signal from the first pressure sensor 46.

The communication unit 59 is controlled by the CPU 100 to transmit predetermined information to an external device via a network 900, or to receive information from an external device via the network 900 and pass the information to the CPU 100. Communication via this network 900 may be either wireless or wired. In this embodiment, the network 900 is the Internet, but not limited to this, it may be another type of network such as a hospital LAN (Local Area Network), or it may be one-to-one communication using a USB cable or the like. The communication unit 59 may include a micro USB connector.

The pump 32 and the valve 33 are connected to the pressing cuff 21 via the air pipe 39, and the second pressure sensor 31 is connected to the pressing cuff 21 via the air pipe 38. Note that the air pipes 39, 38 may be a single common pipe. The second pressure sensor 31 detects pressure inside the pressing cuff 21 via the air pipe 38. In this example, the pump 32 is a piezoelectric pump and supplies air as a pressurizing fluid to the pressing cuff 21 through the air pipe 39 in order to pressurize the pressure in the pressing cuff 21 (cuff pressure). The valve 33 is mounted on the pump 32, and opening and closing of the valve 33 is controlled in accordance with on/off of the pump 32. In other words, when the pump 32 is turned on, the valve 33 closes to enclose air in the pressing cuff 21, and on the other hand, when the pump 32 is turned off, the valve 33 opens so that the air in the pressing cuff 21 is discharged to the atmosphere through the air pipe 39. Note that the valve 33 has the function of a check valve and the discharged air does not flow backward. The pump driving circuit 320 drives the pump 32 based on a control signal given from the CPU 100.

The second pressure sensor 31 is a piezoresistive pressure sensor in this example, and detects, through the air pipe 39, the pressure in the cuff 20 (the pressing cuff 21) with atmospheric pressure being set to a reference (zero) in this example, and outputs the pressure as a time-series signal. The oscillation circuit 310 oscillates based on an electric signal value based on a change in electric resistance due to a piezoresistive effect from the second pressure sensor 31, and outputs a frequency signal having a frequency corresponding to the electric signal value of the second pressure sensor 31 to the CPU 100. In this example, the output of the second pressure sensor 31 is used to control the pressure in the pressing cuff 21.

Like the oscillation circuit 310, the oscillation circuit 460 receiving the output of the first pressure sensor 46 of the sensor assembly 40 oscillates based on an electric signal value based on a change in electric resistance due to a piezoresistive effect from the first pressure sensor 46, and outputs a frequency signal having a frequency corresponding to the electric signal value of the first pressure sensor 46 to the CPU 100. In this example, the output of the first pressure sensor 46 is used to calculate blood pressure values (including systolic blood pressure and diastolic blood pressure) by an oscillometric method. The output of the first pressure sensor 46 can be processed by a detection system of the same kind as a pressure detection system based on the existing oscillometric method. Therefore, the sphygmomanometer 1 can be easily designed.

The battery 53 supplies power to elements mounted on the main body 10, in this example, the elements including the CPU 100, the second pressure sensor 31, the pump 32, the valve 33, the display unit 50, the memory 51, the communication unit 59, the oscillation circuits 310, 460, and the pump driving circuit 320. The battery 53 also supplies power to the first pressure sensor 46 of the sensor assembly 40 through the wiring line 71.

(Operation of Blood Pressure Measurement)

When the sphygmomanometer 1 is worn on the left wrist 90, in a state in which engagement between the one end 20e side (the inner peripheral side) and the other end 20f side (the outer peripheral side) of the cuff 20 is released, a user puts a left hand through the cuff 20 in a direction indicated by an arrow A shown in FIG. 1. Then, as shown in FIG. 2, the user adjusts an angular position of the cuff 20 around the left wrist 90 to position the alignment mark 29 (see FIG. 1) of the cuff 20 on the radial artery 91 passing through the left wrist 90. As a result, the sensor assembly 40 comes into contact with the artery passing portion 90a of the left wrist 90. In this state, the user adjusts a ring length of the cuff 20 so as to exactly match a peripheral length of his/her left wrist 90, and fixes the one end 20e side (the inner peripheral side) and the other end 20f side (the outer peripheral side) of the cuff 20 by the hook-and-loop fastener 24. In this way, the sphygmomanometer 1 is worn on the left wrist 90.

Figure 6:
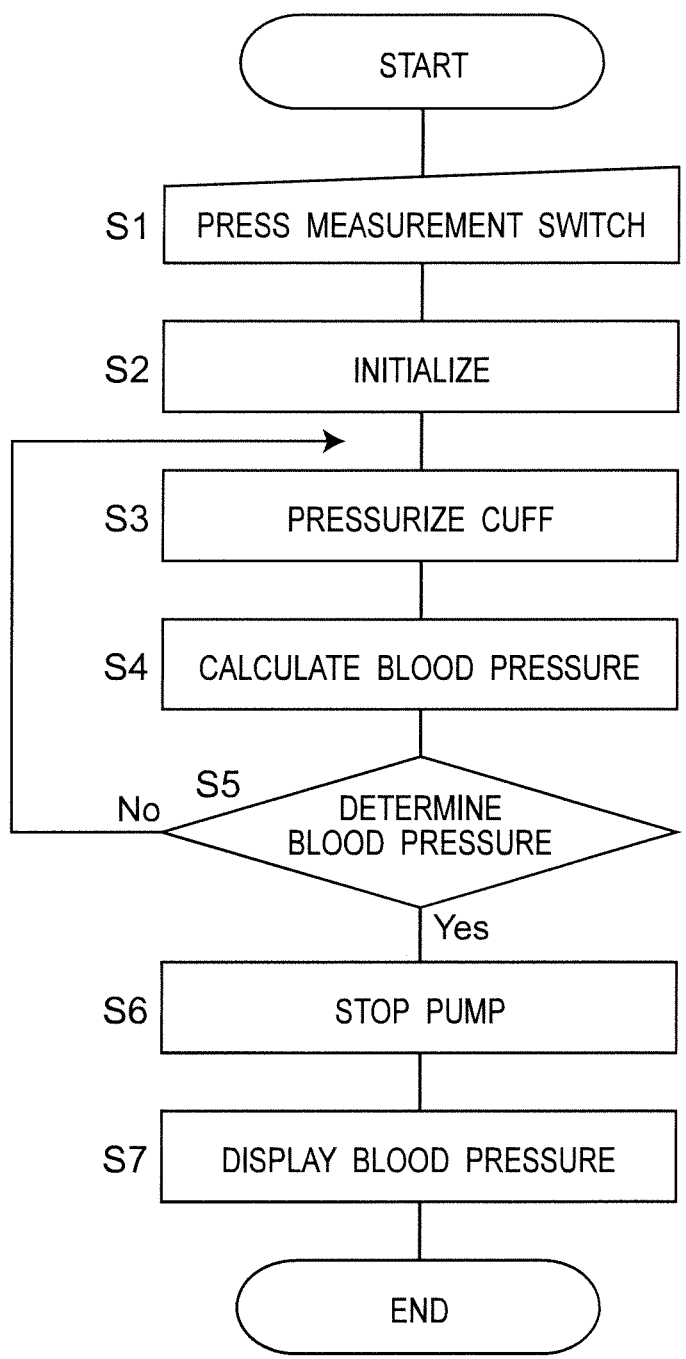
FIG. 6 is a flowchart showing an operation flow when the sphygmomanometer performs blood pressure measurement.

FIG. 6 shows an operation flow when the sphygmomanometer 1 performs the blood pressure measurement. When the user presses the push type switch as the operation unit 52 provided on the main body 10 (step S1), the CPU 100 initializes a processing memory area (step S2). In addition, the CPU 100 turns off the pump 32 via the pump driving circuit 320, opens the valve 33, and exhausts the air in the pressing cuff 21. Subsequently, control is performed to adjust the second pressure sensor 31 and the first pressure sensor 46 to 0 mmHg.

Figure 7:
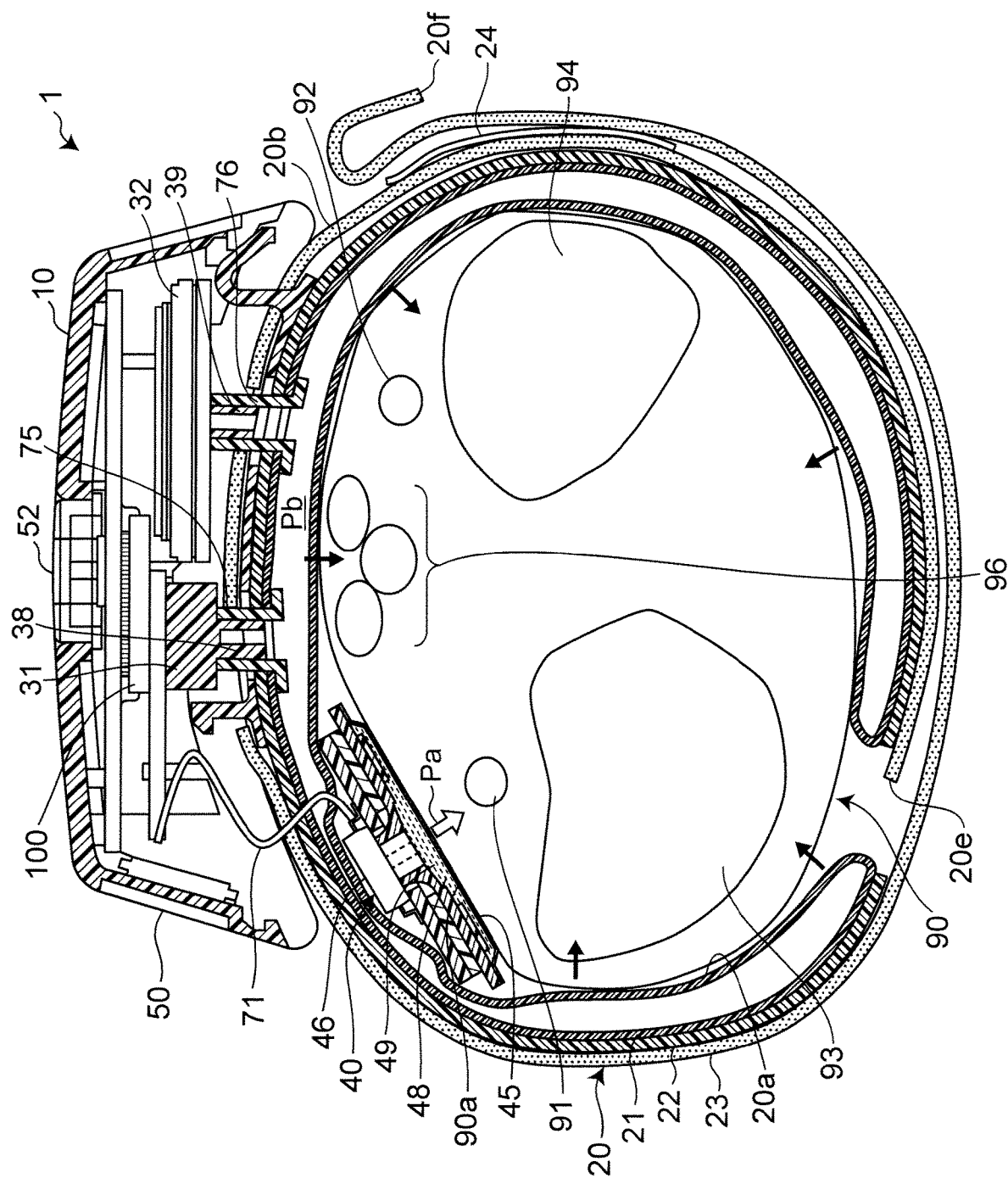
FIG. 7 is a view showing a state in which an artery passing portion of the left wrist serving as a part to be measured is pressed by the pressing cuff via the sensor assembly.

Next, the CPU 100 turns on the pump 32 via the pump driving circuit 320, closes the valve 33, and starts pressurizing the pressing cuff 21 (step S3). In a pressurization process, while pressure Pb (see FIG. 7) of the pressing cuff 21 is monitored by the second pressure sensor 31, the pump 32 is driven via the pump driving circuit 320 to send air to the pressing cuff 21. As a result, the pressing cuff 21 is expanded and the pressure Pb is gradually pressurized. Further, in this pressurization process, in order to calculate the blood pressure values, the CPU 100 monitors pressure Pa (see FIG. 7) of the artery passing portion 90a of the left wrist 90 by the first pressure sensor 46 of the sensor assembly 40, and acquires a pulse wave signal as a fluctuation component.

At this time, in the sensor assembly 40, pressure of the incompressible fluid 49 disposed facing the artery passing portion 90a of the left wrist 90 via the film 45 coincides with the pressure Pa applied to the artery passing portion 90a of the left wrist 90. Since the incompressible fluid 49 has substantially no (negligible) volume change, the pressure Pa applied to the artery passing portion 90a of the left wrist 90 can be transmitted to the first pressure sensor 46 as it is without pressure loss. Therefore, the first pressure sensor 46 can detect the pressure of the fluid 49 as the pressure Pa applied to the artery passing portion 90a of the left wrist 90.

Next, in step S4 in FIG. 6, the CPU 100 applies a known algorithm by the oscillometric method based on the pulse wave signal acquired at this point to calculate the blood pressure values (systolic blood pressure SBP and diastolic blood pressure DBP).

At this point in time, if the blood pressure values cannot be calculated yet due to insufficient data (NO in step S5), unless the cuff pressure reaches upper limit pressure (preset to, for example, 300 mmHg for safety), processing of steps S3 to S5 is repeated.

When the blood pressure values can be calculated in this manner (YES in step S5), the CPU 100 stops the pump 32, opens the valve 33, and exhausts the air in the pressing cuff 21 (step S6). Finally, a measurement result of the blood pressure values is displayed on the display unit 50 (step S7).

In this manner, in the sphygmomanometer 1, the first pressure sensor 46 of the sensor assembly 40 detects the pressure Pa itself applied to the artery passing portion 90a of the left wrist 90, separately from the pressing cuff 21. Therefore, even when the pressing cuff 21 expands greatly in the thickness direction at the time of pressurization and compression loss occurs as a result of setting the cuff width dimension (equal to the width direction dimension of the pressing cuff 21 in a natural state (below, the same.)) to be small (for example, about 25 mm), the blood pressure can be measured with high accuracy.

Figure 8A:
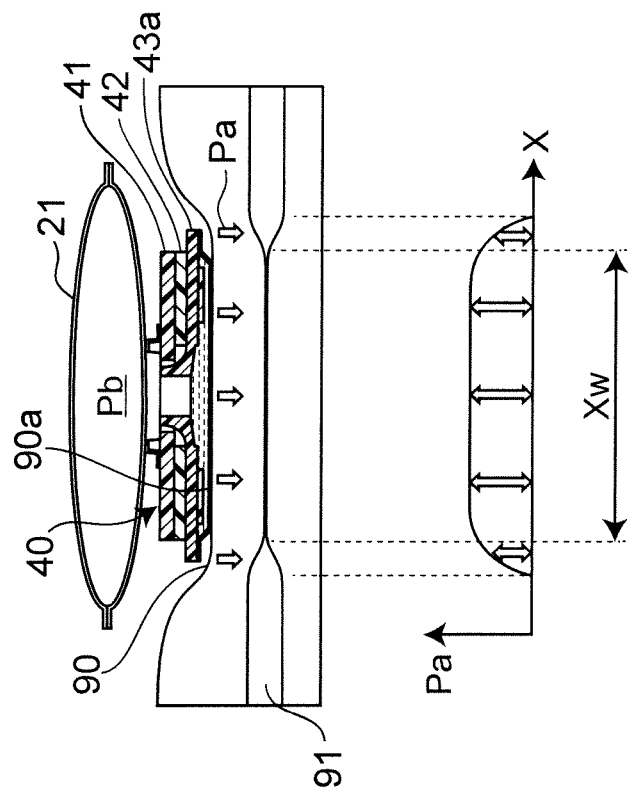
FIG. 8A is a diagram showing a pressure distribution along the cuff width direction when the sensor assembly is omitted in the blood pressure measuring cuff, as compared with FIG. 8B.
Figure 8B:
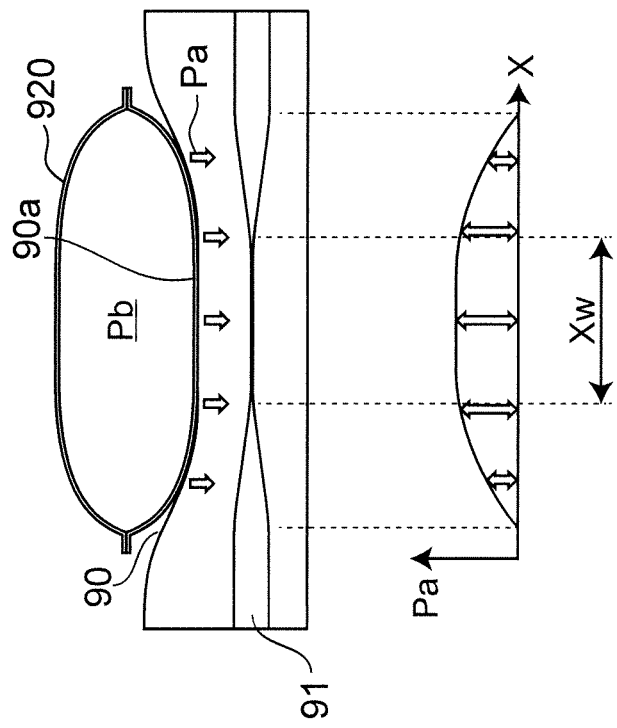
FIG. 8B is a diagram showing a pressure distribution along a cuff width direction when the artery passing portion of the left wrist serving as the part to be measured is pressed by the blood pressure measuring cuff.

Further, as shown in an upper part of FIG. 8A, as a result of setting the cuff width dimension to be small (for example, about 25 mm), the pressing cuff 21 greatly expands in the thickness direction at the time of pressurization and its cross section is close to a circular shape from an elliptical shape. In this case, as it is (if the plate members 41, 42, 43a are not present), only a part of the cross section close to the circular shape of the pressing cuff 21 which is in contact with the left wrist 90 in the longitudinal direction (corresponding to the X direction, that is, the cuff width direction) of the left wrist 90 contributes to the compression. For this reason, as shown in a lower part of FIG. 8A, a compression range (a range where the pressure Pa is high) Xw is narrowed in the longitudinal direction (the X direction) of the left wrist 90, and the artery passing portion 90a of the left wrist 90 cannot be effectively compressed (the radial artery 91 cannot be completely collapsed). Here, in this sphygmomanometer 1, as shown in an upper part of FIG. 8B, the plate members 41, 42, 43a each having a flat shape along the longitudinal direction (the X direction) of the left wrist 90 are disposed as parts of the sensor assembly 40 on a side opposite to the left wrist 90 along the film 45. Moreover, the reinforcing plate 42 has rigidity. Therefore, as shown in a lower part of FIG. 8B, the compression range Xw is secured widely in the longitudinal direction (the X direction) of the left wrist 90 by these plate members 41, 42, 43a. As a result, the blood pressure can be measured more accurately.

(Verification Result)

Figure 9A:
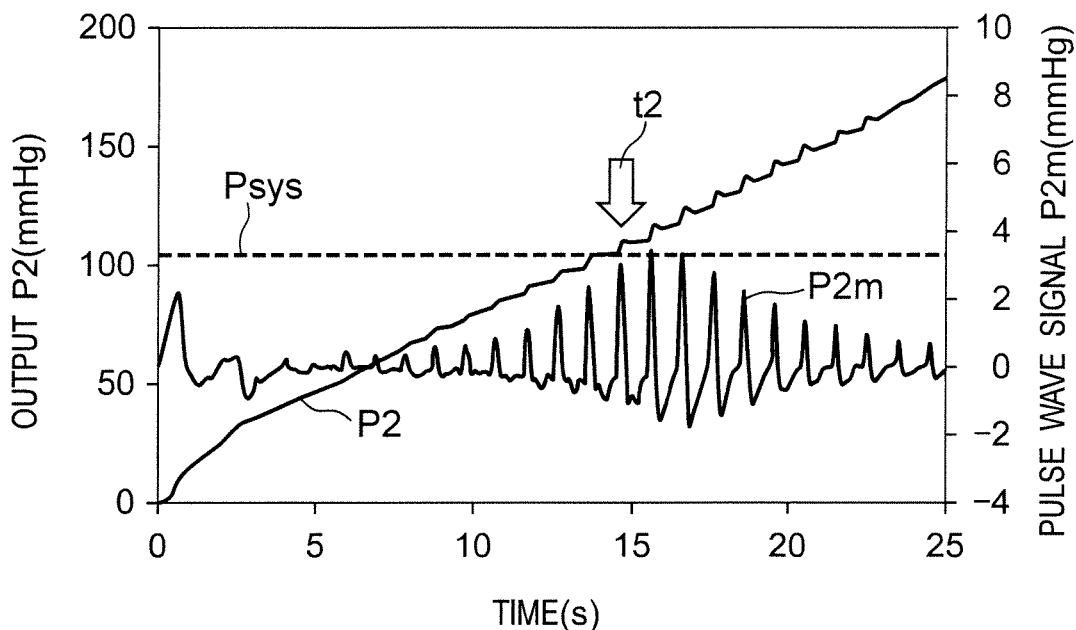
FIG. 9A is a graph showing a pulse wave waveform observed by using an output of a second pressure sensor that detects pressure of the pressing cuff
Figure 9B:
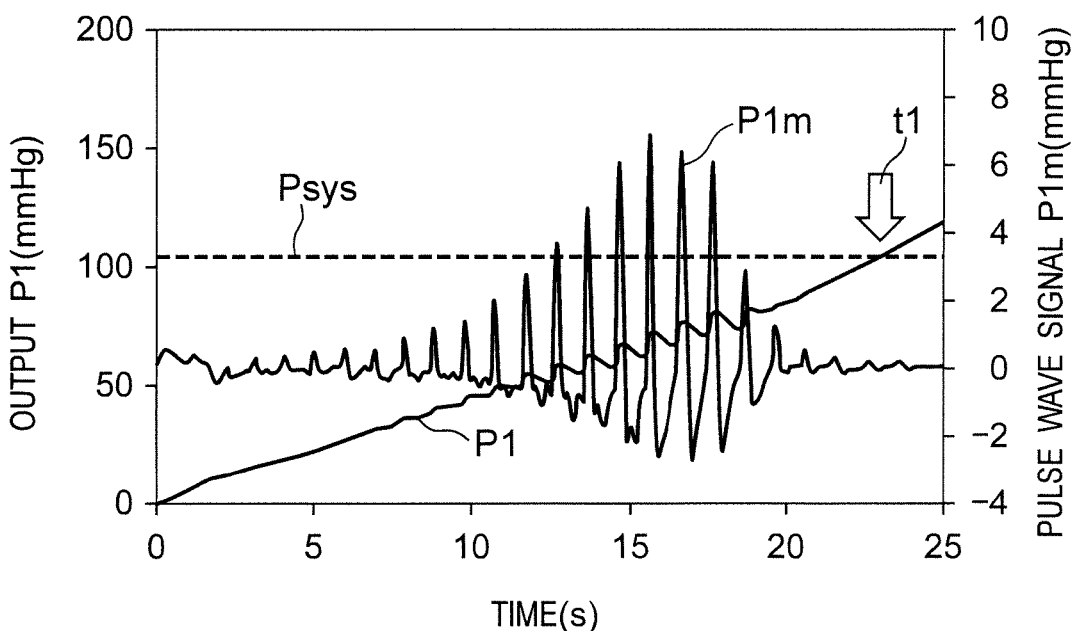
FIG. 9B is a graph showing a pulse wave waveform observed by using an output of a first pressure sensor included in the sensor assembly.

FIG. 9A shows a pulse wave signal P2m observed using an output P2 of the second pressure sensor 31 that detects the pressure Pb of the pressing cuff 21 for a certain subject. FIG. 9B shows a pulse wave signal P1m observed using an output P1 of the first pressure sensor 46 included in the sensor assembly 40 for the subject at the same time. In each of FIGS. 9A and 9B, systolic blood pressure Psys measured by a standard (accurate) sphygmomanometer is shown for the subject at the same time. At a time point t2 where the output P2 of the second pressure sensor 31 matches Psys in FIG. 9A, the pulse wave signal P2m has not yet converged. The pulse wave signal P2m converges at a time point of t≈25 s. Therefore, if it is assumed that the output P2 of the second pressure sensor 31 is used for calculating the blood pressure value, the blood pressure value is observed higher than actual blood pressure, and a measurement error becomes large. On the other hand, the pulse wave signal P1m converges at a time point t1 where the output P1 of the first pressure sensor 46 coincides with Psys in FIG. 9B. Therefore, by using the output P1 of the first pressure sensor 46 included in the sensor assembly 40 for calculating the blood pressure value, measurement accuracy can be improved.

Figure 10A:
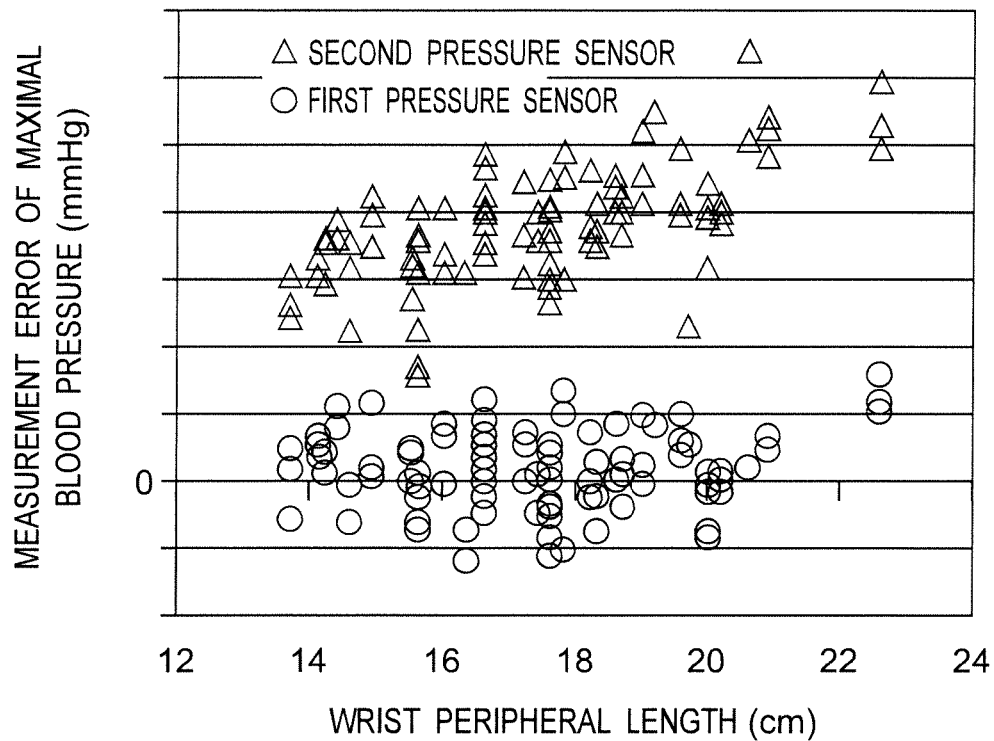
FIG. 10A is a graph showing measurement errors of maximal blood pressure (systolic blood pressure) calculated by using the outputs of the second pressure sensor and the first pressure sensor, for various subjects with different peripheral lengths of wrists.
Figure 10B:
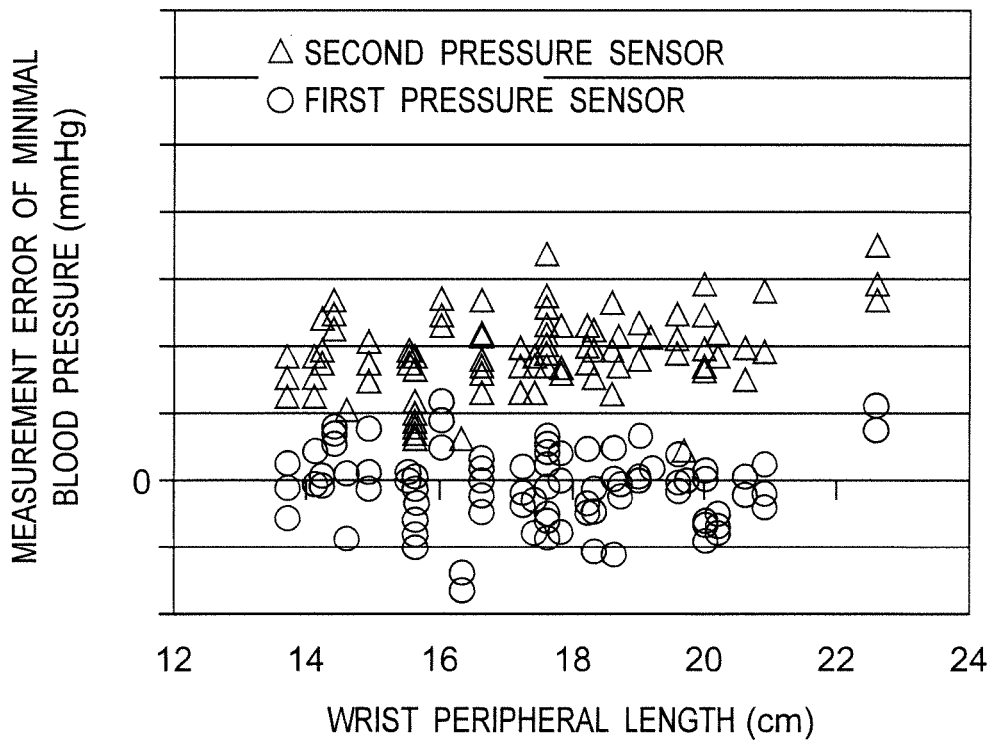
FIG. 10B is a graph showing a measurement errors of minimal blood pressure (diastolic blood pressure) calculated by using the outputs of the second pressure sensor and the first pressure sensor, for various subjects with different peripheral lengths of wrists.

Further, FIG. 10A shows measurement errors of maximal blood pressure (systolic blood pressure) calculated by using the output P2 of the second pressure sensor 31 and the output P1 of the first pressure sensor 46, for various subjects with different peripheral lengths of the left wrists 90. Similarly, FIG. 10B shows measurement errors of minimal blood pressure (diastolic blood pressure) calculated by using the output P2 of the second pressure sensor 31 and the output P1 of the first pressure sensor 46, for various subjects with different peripheral lengths of the left wrists 90. Here, (measurement error)=(blood pressure value calculated using output P2 or output P1)−(blood pressure value measured by standard sphygmomanometer). As can be seen from FIG. 10A, as compared with the measurement errors of the maximal blood pressure calculated by using the output P2 of the second pressure sensor 31 (individual data is indicated by a triangle), the measurement errors of the maximal blood pressure calculated by using the output Pb of the first pressure sensor 46 (individual data is indicated by a circle) are small. Similarly, as can be seen from FIG. 10B, as compared with the measurement errors of the minimal blood pressure calculated by using the output P2 of the second pressure sensor 31 (individual data is indicated by a triangle), the measurement errors of the minimal blood pressure calculated by using the output P1 of the pressure sensor 46 (individual data is indicated by a circle) are small.

From these verification results, according to the blood pressure measuring cuff 20 and the sphygmomanometer 1 of the present invention, it can be confirmed that the blood pressure can be accurately measured even when the cuff width dimension is set to be small (for example, about 25 mm).

Modified Example

Figure 11:
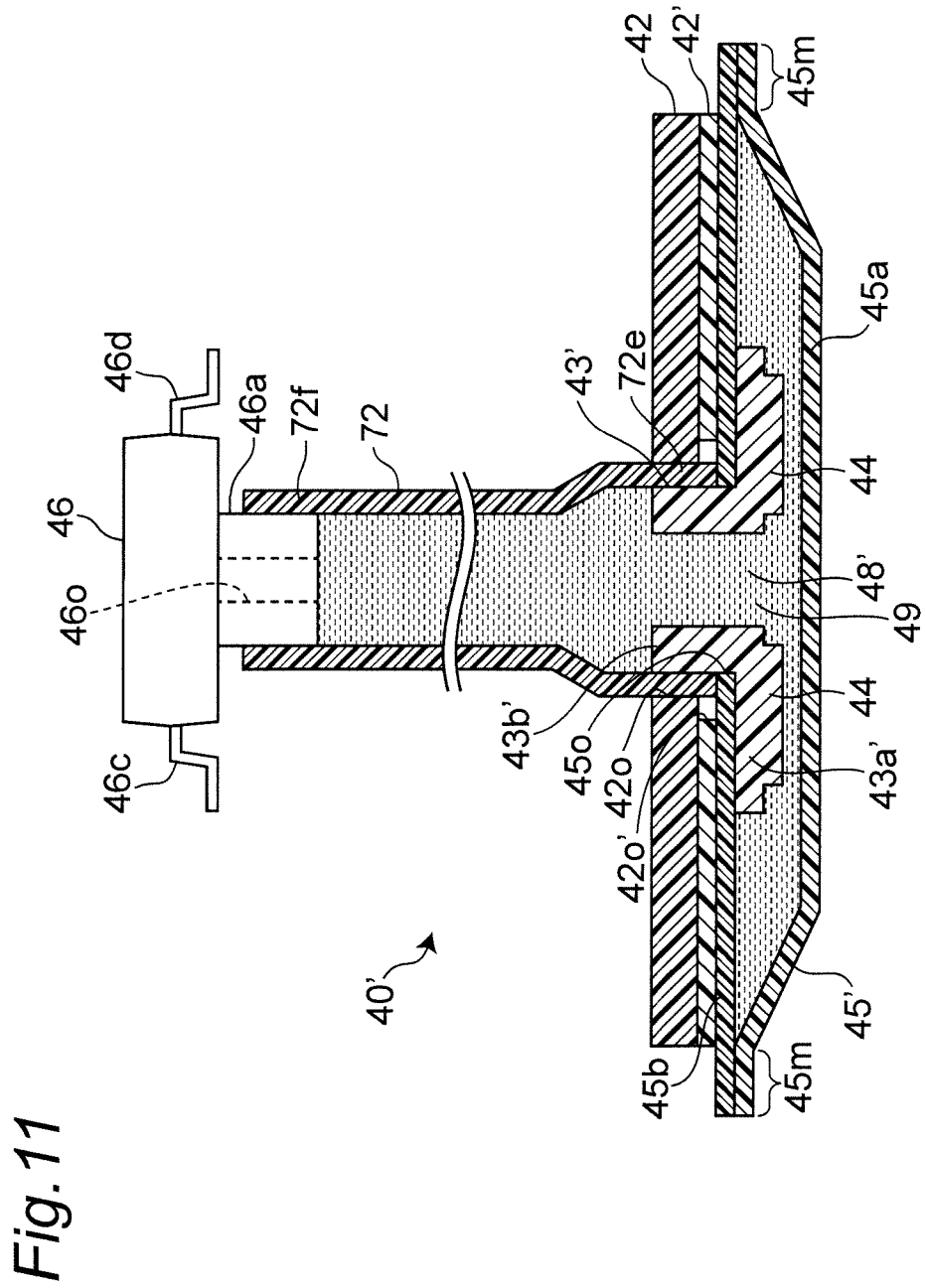
FIG. 11 is a view showing in detail a structure of a sensor assembly of a modified example modified from the above-described sensor assembly.

FIG. 11 shows a structure of a sensor assembly (denoted by reference numeral 40') of a modified example modified from the sensor assembly 40 described above. Note that, in FIG. 11, the same reference numerals are attached to the same constituent elements as those in FIG. 4.

The sensor assembly 40' includes a flat reinforcing plate 42, an adhesive layer 42', a film 45b, a joint member 43', and a film 45a in an order from a side attached to the inner peripheral surface 20a of the pressing cuff 21.

In this example, the reinforcing plate 42 is made of a rigid hard resin having a thickness of about 1 mm and is provided to enhance rigidity of the sensor assembly 40' as a whole. A circular through hole 42o is provided substantially at a center of the reinforcing plate 42.

The adhesive layer 42' is provided for attaching the reinforcing plate 42 and the film 45b. A through hole 42o' is provided concentrically with the through hole 42o of the reinforcing plate 42 substantially at a center of the adhesive layer 42'.

In this example, the film 45b is made of a polyurethane sheet (thickness t=0.15 mm).

The joint member 43' has a plate part 43a' attached along the reinforcing plate 42 and a substantially cylindrical connecting tube part 43b' extending from an approximate center of the plate part 43a' to an outer surface (an upper surface in FIG. 11) level of the reinforcing plate 42 through the through hole 42o of the reinforcing plate 42. On a surface of the plate part 43a' of the joint member 43' on the film 45a side, a spacer 44 for securing a gap between the plate part 43a' and the film 45a is protruded.

In this example, the film 45a is made of a polyurethane sheet (thickness t=0.15 mm) in the same manner as the film 45b. A peripheral edge 45m of the film 45a is welded to a peripheral edge of the film 45b. The films 45a and 45b constitute a fluid bag 45'.

One end 72e of an elongated cylindrical flexible tube 72 is fluid-tightly (liquid-tightly in this example) fitted around the connecting tube part 43b' of the joint member 43' through the through hole 42o of the reinforcing plate 42 and the through hole 42o' of the adhesive layer 42'.

The flexible tube 72 is elongated in a direction opposite to the film 45a with respect to the reinforcing plate 42. Another end (a tip) 72f of the flexible tube 72 is fluid-tightly (liquid-tightly in this example) fitted around the introduction tube part 46a of the first pressure sensor 46. This flexible tube 72 increases a degree of freedom in arrangement of the first pressure sensor 46.

With such a configuration, a sealed fluid chamber 48' is constituted by the film 45a, the joint member 43', the flexible tube 72, and the introduction tube part 46a and the main part 46b of the first pressure sensor 46. In this fluid chamber 48', the pressure transmitting fluid 49 is accommodated. The fluid 49 is an incompressible fluid, which in this example consists of water or silicone oil.

Figure 12:
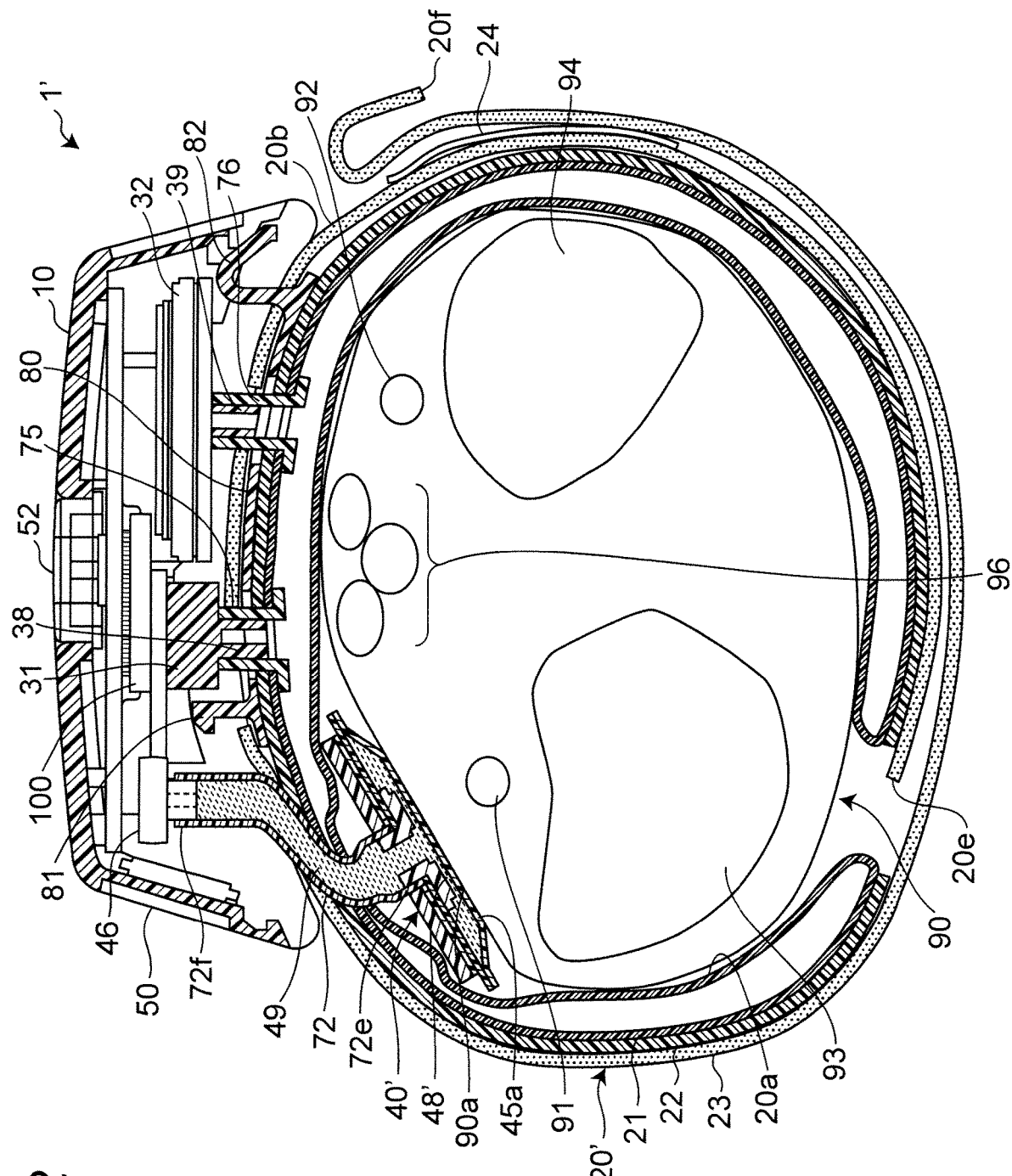
FIG. 12 is a view showing a cross-sectional structure of a sphygmomanometer provided with a blood pressure measuring cuff including the sensor assembly of the modified example in a state of being worn on the left wrist.

FIG. 12 shows a sphygmomanometer 1' provided with a cuff 20' including the sensor assembly 40' in a state of being worn on the left wrist 90. In this example, it is assumed that a space for accommodating the first pressure sensor 46 and a connector (not shown) to which lead terminals 46c, 46d are connected are provided in the main body 10. Further, when attaching the main body 10 to the cuff 20', the first pressure sensor 46 and the flexible tube 72 connected to the first pressure sensor 46 are guided into the main body 10 through through holes previously provided in the pressing cuff 21, the curler 22, and the outer cloth 23 (or by bypassing the pressing cuff 21, the curler 22, and the outer cloth 23). The first pressure sensor 46 is accommodated in the main body 10, and the lead terminals 46c and 46d are connected to the connector.

As can be clearly seen from FIG. 12, in the worn state, the fluid 49 is disposed facing the artery passing portion (in this example, the portion through which the radial artery 91 passes) 90a of the left wrist 90 via the film 45a which forms a part of an outer wall of the fluid chamber 48'. The first pressure sensor 46 detects pressure applied to the artery passing portion 90a of the left wrist 90 via the film 45a and the fluid 49.

In this example, the reinforcing plate 42 and the plate part 43a' of the joint member 43' included in the sensor assembly 40' constitute a plate member having a flat shape. As a result, these plate members 42, 43a' can appropriately press the artery passing portion 90a of the left wrist 90.

Further, the reinforcing plate 42 and the adhesive layer 42' have the through holes 42o, 42o' respectively, and the connecting tube part 43b' of the joint member 43' passing through these through holes 42o, 42o' works as a through hole through which the fluid 49 can flow. Thus, even in a case where the first pressure sensor 46 is disposed in the main body 10 as in this example, the first pressure sensor 46 can detect the pressure applied to the artery passing portion 90a of the left wrist 90 as pressure of the fluid 49 through the through holes 42o, 42o' and the connecting tube part 43b', and through the flexible tube 72. Therefore, presence of the plate members 42, 43a' does not prevent detection of the pressure by the first pressure sensor 46.

In the sphygmomanometer 1', as well as in the above-described sphygmomanometer 1, the first pressure sensor 46 detects the pressure Pa itself applied to the artery passing portion 90a of the left wrist 90, separately from the pressing cuff 21. Therefore, even when the pressing cuff 21 greatly expands in a thickness direction at the time of pressurization and compression loss occurs as a result of setting a cuff width dimension to be small (for example, about 25 mm), blood pressure can be accurately measured.

Moreover, in the sphygmomanometer 1', since the sensor assembly 40' does not include the first pressure sensor 46 and the wiring substrate 41, it is possible to reduce a dimension in a thickness direction of the sensor assembly 40' (accordingly, the cuff 20').

The sensor assembly 40 described above integrally includes the plate members 41, 42, 43a, and the sensor assembly 40' integrally includes the plate members 42, 43a', but is not limited thereto. Separately from the sensor assembly 40, 40', a plate member having a flat shape along a longitudinal direction of the left wrist 90 may be provided between the sensor assembly 40 and the pressing cuff 21. Even with such a plate member, a compression range is secured widely with respect to the longitudinal direction of the wrist. As a result, the blood pressure can be measured more accurately.

Further, in the above embodiment, the pressure transmitting fluid 49 is an incompressible fluid, but the present invention is not limited thereto. For example, the pressure transmitting fluid 49 may be a compressible gas such as air.

Further, in the above-described embodiment, the pressure control of the pressing cuff 21 is performed using the output of the second pressure sensor 31, but the present invention is not limited thereto. Not only the calculation of the blood pressure value but also the pressure control of the pressing cuff 21 may be performed using the output of the first pressure sensor 46. In that case, the second pressure sensor 31 and the oscillation circuit 310 can be omitted. As a result, it is possible to reduce the size and cost of the sphygmomanometer 1, 1'.

Further, in the above embodiment, it is assumed that the sphygmomanometer 1, 1' is to be worn on the left wrist 90. However, the present invention is not limited to this. For example, in FIG. 1, it is assumed that a user passes a right hand through the cuff 20 from a side opposite to the arrow A. Thus, the sphygmomanometer 1, 1' can be conveniently used by left-handed users. Further, the part to be measured may be a part other than the wrist (for example, an upper arm).

As is described above, the present disclosure provides a sensor assembly, in a blood pressure measuring cuff including a pressing cuff which is belt-like, wound around a part to be measured, and receives supply of a pressurizing fluid to press the part to be measured, and the sensor assembly disposed at a portion of an inner peripheral surface of the pressing cuff which should face an artery of the part to be measured to detect pressure applied to an artery passing portion of the part to be measured by the pressing cuff, separately from the pressing cuff, the sensor assembly comprising:
 a fluid chamber;
 a pressure transmitting fluid accommodated in the fluid chamber; and
 a pressure sensor for detecting pressure of the pressure transmitting fluid as pressure applied to the artery passing portion of the part to be measured,
wherein the fluid chamber includes a film that forms a part of an outer wall of the fluid chamber and should be brought into contact with the artery passing portion of the part to be measured, a plate member disposed on a side opposite to the part to be measured along the film and having a flat shape along a longitudinal direction of a wrist serving as the part to be measured, and a cylindrical connecting tube part integrally formed with the plate member and extending from the plate member to a side opposite to the part to be measured,
a peripheral edge of the film is welded to a peripheral edge of the plate member,
 the connecting tube part has a through hole that allows the pressure transmitting fluid to flow across the plate member,
 the pressure sensor has a main part for detecting the pressure of the pressure transmitting fluid and a cylindrical introduction tube part for guiding the pressure transmitting fluid to the main part, and
 the introduction tube part of the pressure sensor is fluid-tightly fitted to the connecting tube part directly or via a flexible tube.

In the present specification, the "part to be measured" typically refers to a wrist, but it may be a part other than the wrist (for example, an upper arm). If the part to be measured is a wrist, for example, the "artery passing portion" of the part to be measured refers to a portion through which a radial artery or an ulnar artery passes (including a surface of the wrist).

The "inner peripheral surface" of the pressing cuff refers to a surface, of both surfaces of a belt of the pressing cuff, which faces the part to be measured at the time of wearing.

The "sensor assembly" "to detect pressure applied to an artery passing portion of the part to be measured by the pressing cuff, separately from the pressing cuff" means detecting the pressure itself applied to the artery passing portion of the part to be measured outside the pressing cuff, not the pressure within the pressing cuff (or a space communicating therewith).

The sensor assembly of the present disclosure is disposed at the portion of the inner peripheral surface of the pressing cuff which should face the artery of the part to be measured, and constitutes the blood pressure measuring cuff. The blood pressure measuring cuff thus configured is worn by surrounding the part to be measured (for example, the wrist). In this state, at the time of blood pressure measurement, the pressing cuff receives supply of the pressurizing fluid from outside (for example, a main body of a sphygmomanometer) and presses the part to be measured. At this time, the pressing cuff presses the part to be measured through the sensor assembly. Separately from the pressing cuff, the sensor assembly detects the pressure applied to the artery passing portion of the part to be measured by the pressing cuff. In other words, the sensor assembly detects the pressure itself applied to the artery passing portion of the part to be measured outside the pressing cuff, not the pressure in the pressing cuff (or the space communicating therewith). Based on an output of the sensor assembly, a blood pressure measurement value is obtained by a known method.

In particular, when the pressing cuff presses the part to be measured at the time of measuring the blood pressure, in the sensor assembly, the pressure of the pressure transmitting fluid disposed facing the artery passing portion of the part to be measured via the film coincides with the pressure applied to the artery passing portion of the part to be measured. The pressure of the pressure transmitting fluid is transmitted to the main part of the pressure sensor through the connecting tube part forming the through hole integrally formed with the plate member and the introduction tube part of the pressure sensor fluid-tightly fitted to the connecting tube part directly or via the flexible tube. Presence of the plate member does not prevent detection of the pressure by the pressure sensor. Therefore, the pressure sensor can detect the pressure of the pressure transmitting fluid as the pressure applied to the artery passing portion of the part to be measured.

Thus, the sensor assembly of the present disclosure is suitable for detecting the pressure itself applied to the artery passing portion of the part to be measured. Therefore, even when the pressing cuff is greatly expanded in a thickness direction at the time of pressurization and compression loss occurs as a result of setting a cuff width dimension (equal to a width direction dimension of the pressing cuff in a natural state (below, the same.)) to be small (for example, about 25 mm), blood pressure can be accurately measured.

Also, the output of the sensor assembly (i.e., an output of the pressure sensor) can be processed by a detection system of the same kind as a pressure detection system based on an existing oscillometric method. Therefore, the sphygmomanometer having the blood pressure measuring cuff can be easily designed.

As a result of setting the cuff width dimension small (for example, about 25 mm), when the pressing cuff greatly expands in the thickness direction at the time of pressurization and its cross section becomes close to a circular shape from a flat elliptical shape, as it is (if the plate member is not present), only a part of the cross section close to the circular shape of the cuff, which is in contact with the wrist in the width direction of the cuff contributes to the compression. Therefore, a compression range becomes narrow in the longitudinal direction of the wrist (corresponding to the width direction of the cuff), and there is a possibility that the artery passing portion of the part to be measured cannot be effectively pressed. Here, in the sensor assembly, the plate member having the flat shape along the longitudinal direction of the wrist serving as the part to be measured is disposed on the side opposite to the part to be measured along the film. Therefore, with this plate member, the compression range is secured widely in the longitudinal direction of the wrist. As a result, the blood pressure can be measured more accurately. Further, since a portion of the fluid chamber facing the part to be measured is constituted by the film and the plate member having the flat shape along the film in a state in which the peripheral edges thereof are welded to each other, it is possible to reduce a dimension in the thickness direction of the sensor assembly (hence the cuff).

It should be noted that the "pressure transmitting fluid" is desirably, for example, incompressible fluid such as water or silicone oil. In such a case, even if the pressing cuff is subjected to compression, since the pressure transmitting fluid has substantially no (negligible) volume change, the pressure applied to the artery passing portion of the part to be measured can be transmitted to the pressure sensor as it is without pressure loss.

Note that it is preferable that the sensor assembly is attached to the portion of the inner peripheral surface of the pressing cuff that should face the artery of the part to be measured so as not to fall off from the pressing cuff.

In the sensor assembly of one embodiment, the plate member has a spacer protruding toward the film side for securing a gap between the plate member and the film.

In the sensor assembly of this embodiment, the gap between the plate member and the film can be secured by the spacer.

In the sensor assembly of one embodiment,
the introduction tube part of the pressure sensor is directly fitted to the connecting tube part, and
the plate member includes a wiring substrate, to which a lead terminal protruding from the main part of the pressure sensor is connected, in a state in which the wiring substrate is laminated on a side of the plate member opposite to the part to be measured.

In the sensor assembly of this embodiment, the output of the pressure sensor is output as an electric signal from the wiring substrate laminated on the side of the plate member opposite to the part to be measured via a wiring line. Therefore, as compared with a case where pressure is transmitted by using piping, the output from the sensor assembly to, for example, the main body of the sphygmomanometer can be achieved with a simple configuration and space saving.

In the sensor assembly of one embodiment, a wiring line for outputting an output of the pressure sensor as an electric signal extends from the wiring substrate.

In the sensor assembly of this embodiment, the wiring line for outputting the output of the pressure sensor as the electric signal extends from the wiring substrate. Therefore, wiring work from the sensor assembly to, for example, the main body of the sphygmomanometer is easily performed.

In the sensor assembly of one embodiment, the plate member has rigidity.

In the present specification, "rigidity" does not mean complete rigidity but means rigidity to an extent that deflection can be ignored in application of the blood pressure measuring cuff.

In the sensor assembly of this embodiment, the plate member has rigidity. Therefore, with this plate member, the compression range can be widely secured more reliably in the longitudinal direction of the wrist (corresponding to the width direction of the cuff).

In the sensor assembly of one embodiment, regarding the plate member, a dimension in a circumferential direction along a circumference of a wrist serving as the part to be measured is set within a range of 15 mm to 100 mm, and a dimension in a width direction along a longitudinal direction of the wrist is set within a range of 20 mm to 30 mm.

In the sensor assembly of this embodiment, the plate member can appropriately press the artery passing portion of the wrist (for example, the portion through which the radial artery passes).

As is apparent from the above, the sensor assembly of the present disclosure is suitable for detecting the pressure applied to the artery passing portion of the part to be measured by the pressing cuff, separately from the pressing cuff which presses the part to be measured.

The above-described embodiments are exemplary and various modifications are possible without departing from the scope of the invention. The above-described multiple embodiments can be established separately, but combinations of the embodiments are also possible. Also, the various characteristics of the different embodiments can be established separately, but combinations of the characteristics in the different embodiments are also possible.

The invention claimed is:

1. A sensor assembly, in a blood pressure measuring cuff including a pressing cuff which is belt-like, wound around a part to be measured, and receives supply of a pressurizing fluid to press the part to be measured, and the sensor assembly disposed at a portion of an inner peripheral surface of the pressing cuff which should face an artery of the part to be measured to detect pressure applied to an artery passing portion of the part to be measured by the pressing cuff, separately from the pressing cuff, the sensor assembly comprising:
a fluid chamber;
a pressure transmitting fluid accommodated in the fluid chamber; and
a pressure sensor for detecting pressure of the pressure transmitting fluid as pressure applied to the artery passing portion of the part to be measured, wherein
the fluid chamber includes a film that forms a part of an outer wall of the fluid chamber and configured to be brought into contact with the artery passing portion of the part to be measured, a plate member disposed on a side opposite to the part to be measured along the film and having a flat shape along a longitudinal direction of a wrist serving as the part to be measured, and a cylindrical connecting tube part integrally formed with the plate member and extending from the plate member to a side opposite to the part to be measured,
a peripheral edge of the film is welded to a peripheral edge of the plate member,
the connecting tube part has a through hole that allows the pressure transmitting fluid to flow across the plate member,
the pressure sensor has a main part for detecting the pressure of the pressure transmitting fluid and a cylindrical introduction tube part for guiding the pressure transmitting fluid to the main part,
the introduction tube part of the pressure sensor is fluid-tightly fitted to the connecting tube part directly or via a flexible tube,
the plate member has spacers protruding toward the film for securing a gap between the plate member and the film, and
the spacers extend radially in a shape elongated in a direction perpendicular to a center axis of the through hole along a surface facing the film of the plate member, wherein the gap is between the spacers adjacent to each other and allows fluid communication between the gap and the through hole.

2. The sensor assembly according to claim 1, wherein
the introduction tube part of the pressure sensor is directly fitted to the connecting tube part,
the plate member includes a wiring substrate to which a lead terminal protruding from the main part of the pressure sensor is connected, and
the wiring substrate is laminated on a side of the plate member opposite to the part to be measured.

3. The sensor assembly according to claim 2, wherein
a wiring line for outputting an output of the pressure sensor as an electric signal extends from the wiring substrate.

4. The sensor assembly according to claim 1, wherein
the plate member has rigidity.

5. The sensor assembly according to claim 1, wherein
regarding the plate member, a dimension in a circumferential direction along a circumference of the wrist is within a range of 15 mm to 100 mm, and a dimension in a width direction along a longitudinal direction of the wrist is within a range of 20 mm to 30 mm.

6. A sensor assembly, in a blood pressure measuring cuff including a pressing cuff which is belt-like, wound around a part to be measured, and receives supply of a pressurizing fluid to press the part to be measured, and the sensor assembly disposed at a portion of an inner peripheral surface of the pressing cuff which should face an artery of the part to be measured to detect pressure applied to an artery passing portion of the part to be measured by the pressing cuff, separately from the pressing cuff, the sensor assembly comprising:
a fluid chamber;
a pressure transmitting fluid accommodated in the fluid chamber; and
a pressure sensor for detecting pressure of the pressure transmitting fluid as pressure applied to the artery passing portion of the part to be measured, wherein
the fluid chamber includes a film that forms a part of an outer wall of the fluid chamber and configured to be brought into contact with the artery passing portion of the part to be measured, a plate member disposed on a side opposite to the part to be measured along the film and having a flat shape along a longitudinal direction of a wrist serving as the part to be measured, and a cylindrical connecting tube part integrally formed with the plate member and extending from the plate member to a side opposite to the part to be measured,
a peripheral edge of the film is welded to a peripheral edge of the plate member,
the connecting tube part has a through hole that allows the pressure transmitting fluid to flow across the plate member,
the pressure sensor has a main part for detecting the pressure of the pressure transmitting fluid and a cylindrical introduction tube part for guiding the pressure transmitting fluid to the main part,
the introduction tube part of the pressure sensor is fluid-tightly fitted to the connecting tube part directly or via a flexible tube,
the plate member has a plurality of spacers protruding toward the film for securing a gap between the plate member and the film, and
the plurality of spacers (i) extend radially in a shape elongated in a direction perpendicular to a center axis of the through hole along a surface facing the film of the plate member, and (ii) are spaced from each other to allow fluid communication between the gap and the through hole by having the pressure transmitting fluid flow along the surface through the gap between the spacers adjacent to each other.

7. The sensor assembly according to claim 6, wherein
the introduction tube part of the pressure sensor is directly fitted to the connecting tube part, the plate member includes a wiring substrate to which a lead terminal protruding from the main part of the pressure sensor is connected, and the wiring substrate is laminated on a side of the plate member opposite to the part to be measured.

8. The sensor assembly according to claim 7, wherein a wiring line for outputting an output of the pressure sensor as an electric signal extends from the wiring substrate.

9. The sensor assembly according to claim 6, wherein the plate member has rigidity.

10. The sensor assembly according to claim 6, wherein regarding the plate member, a dimension in a circumferential direction along a circumference of the wrist is within a range of 15 mm to 100 mm, and a dimension in a width direction along a longitudinal direction of the wrist is within a range of 20 mm to 30 mm.

\* \* \* \* \*